United States Patent
Kumar et al.

(10) Patent No.: US 9,862,712 B2
(45) Date of Patent: Jan. 9, 2018

(54) BENZIMIDAZOLE BASED EGFR INHIBITORS

(71) Applicant: COUNCIL OF SCIENTIFIC & INDUSTRIAL RESEARCH, Rafi Marg New Delhi (IN)

(72) Inventors: Pradeep Kumar, Pune (IN); Jignesh Kantilal Parikh, Pune (IN); Eeshwaraiah Begari, Pune (IN)

(73) Assignee: Council of Scientific & Industrial Research, Rafi Marg New Delhi (IN)

( * ) Notice: Subject to any disclaimer, the term of this patent is extended or adjusted under 35 U.S.C. 154(b) by 0 days.

(21) Appl. No.: 15/528,592

(22) PCT Filed: Nov. 20, 2015

(86) PCT No.: PCT/IN2015/050172
§ 371 (c)(1),
(2) Date: May 22, 2017

(87) PCT Pub. No.: WO2016/079763
PCT Pub. Date: May 26, 2016

(65) Prior Publication Data
US 2017/0267671 A1    Sep. 21, 2017

(30) Foreign Application Priority Data
Nov. 20, 2014  (IN) .......................... 3370/DEL/2014

(51) Int. Cl.
*C07D 417/04*    (2006.01)
(52) U.S. Cl.
CPC .................... *C07D 417/04* (2013.01)
(58) Field of Classification Search
CPC ................................................. C07D 417/04
See application file for complete search history.

(56) References Cited

U.S. PATENT DOCUMENTS

2004/0157845 A1 *  8/2004  Doherty ............... C07D 233/90
                                                         514/242

OTHER PUBLICATIONS

Golub et al., Science, vol. 286, Oct. 15, 1999, pp. 531-537.*
Shital V. Gandhe et al., "Synthesis and Antimicrobial Activity of 3-Amino-5-aryl/alkylimino-1,2,4-thiadiazolines", Asian Journal of Chemistry, 2008, vol. 20, pp. 32-36.
Li.Y et al., "Discovery of Benzimidazole Derivatives as Novel Multi-Target EGFR, VEGFR-2 and PDGFR Kinase Inhibitors", Bioorganic & Medicinal Chemistry, vol. 19, 2011, pp. 4529-4535.
Sun.N et al., "A General and Facile One-Pot Process of Isothiocyanates from Amines Under Aqueous Conditions", Beilstein Journal of Organic Chemistry, 2012, vol. 8, pp. 61-70.
Yu-Bin Bai et al., "Synthesis and Antifungal Activity of 2-Chloromethyl-1H-Benzimidazole Derivatives against Phytopathogenic Fungi in Vitro", Journal of Agricultural and Food Chemistry, 2013, vol. 61, pp. 2789-2795.

* cited by examiner

*Primary Examiner* — Laura L. Stockton
(74) *Attorney, Agent, or Firm* — Nixon Peabody LLP; Jeffrey L. Costellia

(57) ABSTRACT

The present invention disclosed a novel EGFR inhibitor compound of formula (I), process for preparation thereof and methods of treating abnormal cell growth in mammals by administering the compounds of formula (I).

Formula (I)

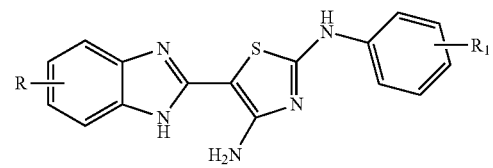

Wherein, R=—H, 3-$CH_3$, 4-$NO_2$, 4-Cl, 2-$CH_3$, 4-$CH_3$, 4-Br, 4-F $R_1$=—H, -4-$OCH_3$, -4-$NO_2$,-2-$NO_2$, -4-Cl, -2,4,6-$CH_3$, -4-$CH_3$, -2-F,4-Br, -4-$CF_3$, -4-S—$CH_3$, -4-Cl,-3-$CF_3$, -3-S—$CH_3$, -3,5-$CF_3$, -2-S—$CH_3$, -3-$CF_3$,-4-$OCF_3$, —Si—$(CH_3)_3$, —Si—$(C_2H_5)_3$, $(CH_3)_2$—Si— $C_2H_5$.

12 Claims, 3 Drawing Sheets

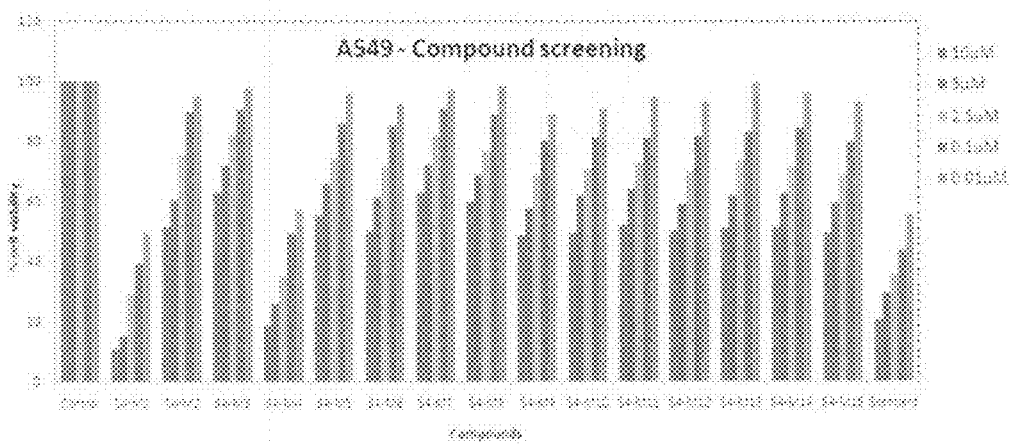
Fig: 1
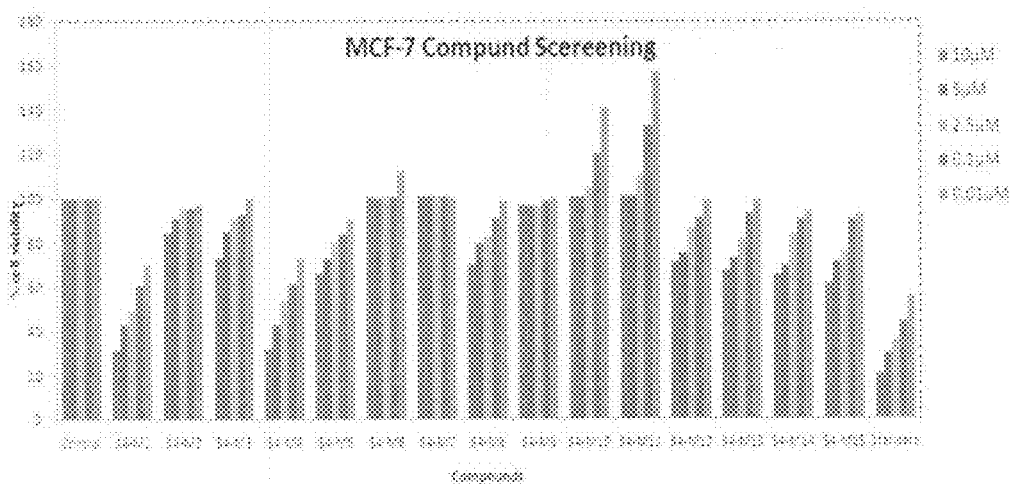
Fig: 2

BENZIMIDAZOLE BASED EGFR INHIBITORS

FIELD OF THE INVENTION

The present invention relates to novel EGFR inhibitor compounds of formula (I), process for preparation thereof and methods for treating abnormal cell growth in mammals by administering the compounds of formula (I). The present invention further relates to formula (I).

BACKGROUND AND PRIOR ART OF THE INVENTION

The identification of (Epidermal Growth Factor Receptor) EGFR as an oncogene led to the development of anticancer therapeutics called "EGFR inhibitors" that includes gefitinib, erlotinib, afatinib, and icotinib for lung cancer, and cetuximab for colon cancer. EGFR is a transmembrane tyrosine kinase receptor that plays a central role in regulating cell division and death.

There is ample literature available on EGFR inhibitor including the compounds having benzimidazole pharmacophore, for example, an article titled "Discovery of benzimidazole derivatives as novel multi-target EGFR, VEGFR-2 and PDGFR kinase inhibitors" by Li. Y et al. *Bioorg Med Chem.*, 2011; 19(15), 4529-35; wherein, 2-Aryl benzimidazole compounds as multi-target EGFR, VEGFR-2 and PDGFR inhibitors are reported.

Article titled "Synthesis of some new Benzimidazole-Thiazole derivatives as anticancer agents" by Z. Nofal et al. published in *Journal of Heterocyclic Chemistry*, 2014; 51(6), 1797-1806 reports synthesis of some new Benzimidazole-Thiazole derivatives as Anticancer Agents. The preparation of Benzimidazole-Thiazole Derivatives involves reaction of 4-(1H-benzo[d]imidazol-2-yl)thiazol-2-amine and its 1-methyl derivative (1) with different reagents such as acid anhydrides, malononitrile, chloroacetyl chloride, and aromatic aldehydes. The cytotoxic activity of some newly synthesized derivatives is studied against two different cell lines HepG2 and PC12.

U.S. Pat. No. 8,815,895 disclosed a method for treating ameliorating ocular neovascular disease, age-related macular degeneration, diabetic retinopathy, retinopathy of prematurity, corneal graft rejection, neovascular glaucoma, epidemic keratoconjunctivitis, malignant glioma, medulloblastoma, pancreatic cancer, lung carcinoma, adenocarcinoma, prostate cancer, or a solid tumor resulting from rhabdomyosarcoma, retinoblastoma, Ewing sarcoma, neuroblastoma, osteosarcoma, acoustic neuroma, neurofibroma, trachoma or pyogenic granuloma, which comprises administering to a patient an effective amount of a compound of formula (I);

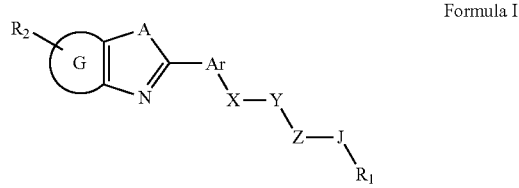

Formula I wherein, as valence and stability permit,
X is —NH—;
Z is a direct bond;
Y represents —C(=O);
A represents O, S, or $NR_7$;
G represents cyclohexane, pyridine, phenyl or phenyl fused with 1,3-dioxolane;
Ar represents phenyl, pyridine, 1,3-thiazole or thiophene, optionally substituted by halogen, lower alkoxy, lower alkyl or halogenated lower alkyl;
$R_1$ represents a disubstituted pyridine ring wherein the substitutents are selected from nitro, cyano, lower alkyl, halogenated lower alkyl, alkenyl, alkynyl, phenylalkyl, amino, alkylamino, acylamino, amido, hydroxyl, alkoxy, acyloxy, carbonyl, phosphoryl, sulfamoyl, sulfate, sulfonamide, sulfonate, sulfoxido, sulfhydryl, and sulfonyl;
$R_2$ represents from 0-4 substituents on the ring to which it is attached wherein the substitutents are selected from halogen, lower alkyl, halogenated lower alkyl, lower alkenyl, 5, 6 or 7-membered single ring aryl, 5, 6 or 7-membered single ring heteroaryl with 1-4 heteroatoms, 3 to 7-membered heterocyclyl with 1-4 heteroatoms, ester, carboxyl, formyl, thioester, thiocarboxylate, thioformate, ketone, aldehyde, amino optionally substituted by alkyl, acylamino, amido, amidino, cyano, nitro, azido, alkylthio, sulfonyl, sulfoxido, sulfate, sulfonate, sulfamoyl, sulfonamido, phosphoryl, phosphonate, phosphinate, —OH, —SH, —$NH_2$, or any two $R_2$, when occurring more than once in a cyclic or polycyclic structure, can be taken together form a 4- to 8-membered cycloalkyl, aryl, or heteroaryl;
$R_7$, represents H, lower alkyl, or lower alkyl substituted by —$CONH_2$, morpholine, piperidine or piperidine N-substituted by —COO-tert-butyl; and
J is absent.

More specifically, the compound of formula (I) described in the document is as shown below:

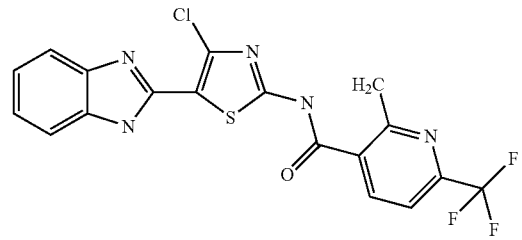 [SMILES: Cc1nc(C(F)(F)F)ccc1C(=O)Nc1nc(Cl)c(-c2nc3ccccc3[nH]2)s1]

Article titled "A general and facile one-pot process of isothiocyanates from amines under aqueous conditions" by N Sun et al. published in *Beilstein J Org Chem.*, 2012, 8, 61-70 reports a general and facile one-pot protocol for the preparation of a broad range of alkyl and aryl isothiocyanates from their corresponding primary amines under aqueous conditions. Article titled "Studies in the chemistry of some new 1,2,4-thiadiazolidine by oxidative cyclisation" by D T Tayade et al. published in *International Journal of Chemistry*, 2010, 2 (2), pp 40-43 reports a novel series of Hector's bases (1,2,4-thiadiazolidine). The 1-substituted-3-formamidinothiocarbamides (1a-f) and 1,3-bis(N-substituted-thioamido)guanidines (1g-l) are oxidatively cyclized by using aqueous bromine as oxidizing agent in chloroform medium to synthesize new series of Hectors bases, viz; 3-imino-5-substituted imino-1,2,4-thiadiazolidine (2a-f) and 3-substituted thioamidoimino-5-substituted imino-1,2,4-thiadiazolidine (2g-l), respectively.

Article titled "Synthesis and Antimicrobial Activity of 3-Amino-5-aryl/alkylimino-1,2,4-thiadiazolines" by S V Gandhe et al. published in *Asian J. Chem.*, 2008, 20(1), pp 32-36 reports 3-amino-5-aryl/alkyl imino-1,2,4-thiadiazolines (IV) synthesized by the oxidative cyclization of 1-amidino-3-aryl/alkyl thiocarbamides (II) with iodine followed by basification.

Article titled "Synthesis and antifungal activity of 2-chloromethyl-1h benzimidazole derivatives against phytopathogenic fungi in vitro" by *J. Agric. Food Chem.*, 2013, 61, 2789-2795 reports a series of 35 benzimidazole derivatives synthesized from 2-chloromethyl-1H-benzimidazole in good yields. They reports synthesis of 2-Chloromethyl-1H-benzimidazole (1) from o-phenylenediamine and chloroacetic acid in presence of HCl. The effectiveness of most anticancer agents is greatly reduced because of their high toxicity and the nature of the illness. It is believed that the problem of high toxicity of the anticancer agents can be circumvented by chemical modifications of those structures in such a way that they act more specifically on tumor cells without increasing systemic toxicity. The research in this field is therefore mainly directed to the synthesis of anticancer agents which would possess high antineoplastic activity, low systemic toxicity and low mutagenicity on normal cells. Preferably, such anticancer agents would possess an extended shelf life without experiencing polymerization or decomposition problems, and could be handled by anyone having minimal knowledge of this subject. Finally, such anticancer agents would be prepared easily in large quantities. Accordingly, the present invention provides novel anti-cancer compounds of formula (I) and process for preparation of the same.

OBJECTIVE OF INVENTION

The main objective of the present invention is to provide a novel anti-cancer compound of formula (I)

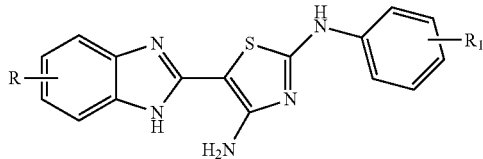

Formula (I)

Wherein, R=—H, 3-$CH_3$, 4-$NO_2$, 4-Cl, 2-$CH_3$, 4-$CH_3$, 4-Br, 4-F $R_1$=—H, -4-$OCH_3$, -4-$NO_2$,-2-$NO_2$, -4-Cl, -2,4,6-$CH_3$, -4-$CH_3$, -2-F,4-Br, -4-$CF_3$, -4-S—$CH_3$, -4-Cl,-3-$CF_3$, -3-S—$CH_3$, -3,5-$CF_3$, -2-S—$CH_3$, -3-$CF_3$,-4-$OCF_3$, —Si—($CH_3$)$_3$, —Si—($C_2H_5$)$_3$, ($CH_3$)$_2$—Si— $C_2H_5$.

Another objective of the present invention is to provide a process for preparation of compounds of formula (I) from substituted 1-phenyl-3-formamidinothiocarbamide and benzoimidazole compound.

Still another objective of the present invention is to provide a method for treating abnormal cell growth in mammals by administering said compound of formula (I) and a pharmaceutical composition for treating such disorders that contain the compound of formula (I).

SUMMARY OF THE INVENTION

Accordingly, the present invention provides novel anti-cancer compounds of formula (I);

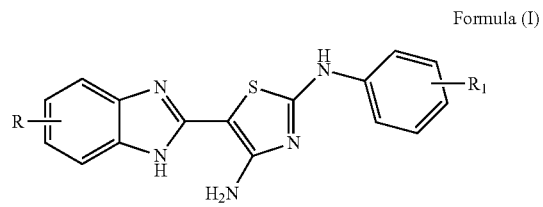

Formula (I)

Wherein, R=—H, 3-$CH_3$, 4-$NO_2$, 4-Cl, 2-$CH_3$, 4-$CH_3$, 4-Br, 4-F $R_1$=—H, -4-$OCH_3$, -4-$NO_2$,-2-$NO_2$, -4-Cl, -2,4,6-$CH_3$, -4-$CH_3$, -2-F,4-Br, -4-$CF_3$, -4-S—$CH_3$, -4-Cl,-3-$CF_3$, -3-S—$CH_3$, -3,5-$CF_3$, -2-S—$CH_3$, -3-$CF_3$,-4-$OCF_3$, —Si—($CH_3$)$_3$, —Si—($C_2H_5$)$_3$, ($CH_3$)$_2$—Si— $C_2H_5$.

In another embodiment, the present invention provides a process for the preparation of compounds of formula (I), wherein said process comprising the steps of:
a) reacting substituted phenyl amine in water with carbon disulfide in presence of suitable base followed by reaction with cyanuric chloride to afford substituted N-Phenyl isothiocynate;
b) reacting the N-Phenyl isothiocynate with guanidine in carbon tetrachloride by refluxing the mixture for the period in the range of 2-4 hrs at temperature in the range of 70° C. to 80° C. to afford substituted 1-phenyl-3-formamidinothiocarbamide;
c) refluxing a solution of chloro acetic acid and ortho-phenylenediamine in HCl for the period in the range of 6-9 hrs at temperature in the range of 90° C. to 100° C. to afford benzimidazole compound;
d) refluxing the solution containing compound of step (b) and compound of step (c) in methanol for the period in the range 4-6 hrs at temperature in the range of 50-70° C. to afford benzimidazole compounds of formula (I).

In preferred embodiment, said substituted phenyl amine compounds are selected from phenyl amine, 4-methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine, 4-bromo-2-fluorobenzenamine.

In another preferred embodiment, said substituted N-Phenyl Isothiocynate compounds are selected from phenyl isothiocynate, 4-methoxy phenyl isothiocynate, 4-nitro phenyl isothiocynate, 2-nitro phenyl isothiocynate, 4-Chloro phenyl isothiocynate, 2-isothiocyanato-1,3,5-trimethylbenzene, 4-bromo-2-fluoro-1-isothiocyanatobenzene.

In yet another preferred embodiment, said substituted 1-phenyl-3-formamidinothiocarbamide compounds are selected from 1-phenyl-3-formamidinothiocarbamide, 4-Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide, 2-Fluro,4-Bromo phenyl-3 formamidinothiocarbamide.

In still another preferred embodiment, said benzoimidazole compound in step (c) is selected from 2-chloromethyl-1H-benzo[d]imidazole, 2-(chloromethyl)-5-methyl-1H-benzo[d]imidazole, 2-(chloromethyl)-4-methyl-1H-benzo[d]imidazole, 2-(chloromethyl)-4-methyl-1H-benzo[d]imidazole.

In an embodiment of the present invention, wherein a pharmaceutical composition comprising compound of formula (I) and at least one pharmaceutically acceptable carrier.

In still another embodiment, the present invention provides a method of treating abnormal cell growth in mammals by administering the compounds of formula (I) and a pharmaceutical composition for treating such disorders that contain the compounds of formula (I).

In a preferred embodiment of the present invention, wherein said subject is human.

BRIEF DESCRIPTION OF THE DRAWINGS

FIG. 1: In vitro screening of Benzimidazole derivatives against A549 cell line indicates % cell Viability after administrating various concentration of synthesized molecules on A549 cell line. 5 dose concentrations were taken in to consideration to find out exact IC50.

FIG. 2: In vitro screening of Benzimidazole derivatives against MCF-7 cell indicates % cell Viability after administrating various concentration of synthesized molecules on MCF-7 cell line. 5 dose concentrations were taken in to consideration to find out exact IC50.

DETAILED DESCRIPTION OF THE INVENTION

Figure 3:
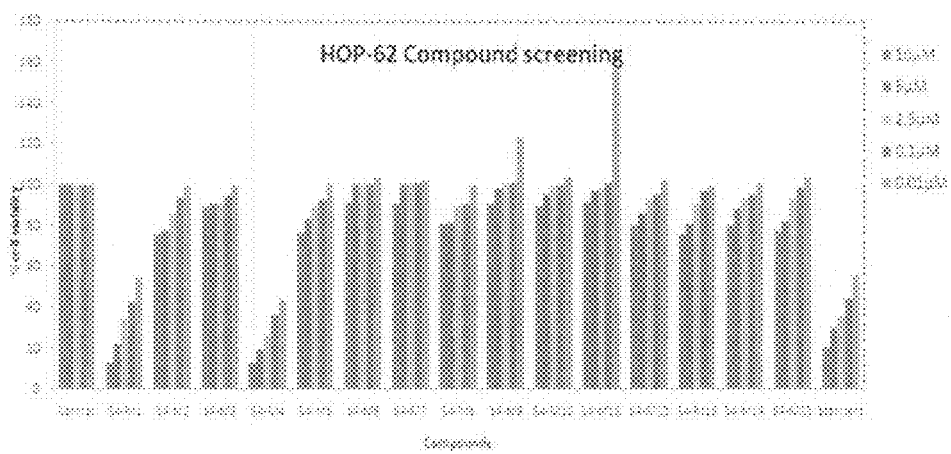
FIG. 3: In vitro screening of Benzimidazole derivatives against HOP-62 cell indicates % cell Viability after administrating various concentration of synthesized molecules on HOP-62 cell line. 5 dose concentrations were taken in to consideration to find out exact IC50.

The invention will now be described in detail in connection with certain preferred and optional embodiments, so that various aspects thereof may be more fully understood and appreciated.

Unless specified otherwise, all technical and scientific terms used herein have the same meaning as commonly understood by one of ordinary skill in the art, to which this invention belongs. Although any methods and materials similar or equivalent to those described herein can be used in the practice or testing of the present invention, the preferred methods and materials are described. To describe the invention, certain terms are defined herein specifically as follows.

Unless stated to the contrary, any of the words "including," "includes," "comprising," and "comprises" mean "including without limitation" and shall not be construed to limit any general statement that it follows to the specific or similar items or matters immediately following it. Embodiments of the invention are not mutually exclusive, but may be implemented in various combinations. The described embodiments of the invention and the disclosed examples are given for the purpose of illustration rather than limitation of the invention as set forth in the appended claims.

In an embodiment, the present invention provides a novel EGFR inhibitor compound of formula (I);

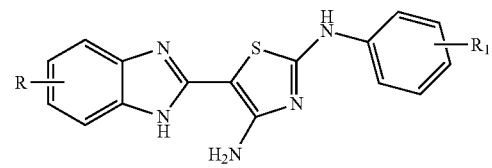

Formula (I)

Wherein, R is selected from hydrogen, alkyl, nitro, halogens such as chlorine, bromine, fluorine and iodine, $R_1$=hydrogen, alkyl, alkoxy, aryl, nitro, halogens such as chlorine, bromine, fluorine and iodine, trifluoromethyl, thioalkyl, trifluromethoxy, Trialkylsilyl.

In preferred embodiment, the present invention provides a novel EGFR inhibitor compound of formula (I).

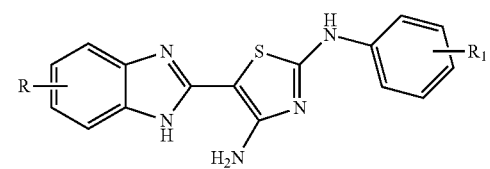

Formula (I)

Wherein, R=—H, 3-$CH_3$, 4-$NO_2$, 4-Cl, 2-$CH_3$, 4-$CH_3$, 4-Br, 4-F $R_1$=—H, -4-$OCH_3$, -4-$NO_2$, -2-$NO_2$, -4-Cl, -2,4,6-$CH_3$, -4-$CH_3$, -2-F,4-Br, -4-$CF_3$, -4-S—$CH_3$, -4-Cl,-3-$CF_3$, -3-S—$CH_3$, -3,5-$CF_3$, -2-S—$CH_3$, -3-$CF_3$,-4-$OCF_3$, —Si—$(CH_3)_3$, —Si—$(C_2H_5)_3$, $(CH_3)_2$—Si—$C_2H_5$.

In another preferred embodiment, the compounds of formula (I) is selected from a. 5-(1H-benzo[d]imidazol-2-yl)-$N^2$-phenylthiazole-2,4-diamine (M1)
b. 5-(1H-benzo[d]imidazol-2-yl)-$N^2$-(4-methoxyphenyl)thiazole-2,4-diamine (M2),
c. 5-(1H-benzo[d]imidazol-2-yl)-$N^2$-(4-nitrophenyl)thiazole-2,4-diamine (M3),
d. 5-(1H-benzo[d]imidazol-2-yl)-$N^2$-(2-nitrophenyl)thiazole-2,4-diamine (M4),
e. 5-(1H-benzo[d]imidazol-2-yl)-$N^2$-(4-chlorophenyl)thiazole-2,4-diamine (M5),
f. 5-(1H-benzo[d]imidazol-2-yl)-$N^2$-mesitylthiazole-2,4-diamine (M6),
g. 5-(1H-benzo[d]imidazol-2-yl)-$N^2$-(4-bromo-2-fluorophenyl)thiazole-2,4-diamine (M7)
h. 5-(1H-benzo[d]imidazol-2-yl)-N2-(3-(trifluoromethyl)phenyl)thiazole-2,4-diamine (M8)
i. 5-(1H-benzo[d]imidazol-2-yl)-N2-p-tolylthiazole-2,4-diamine (M9)
j. 5-(5-methyl-1H-benzo[d]imidazol-2-yl)-N2-phenylthiazole-2,4-diamine (M10)
k. $N^2$-(4-methoxyphenyl)-5-(5-methyl-1H-benzo[d]imidazol-2-yl)thiazole-2,4-diamine (M11)
l. $N^2$-(4-chlorophenyl)-5-(5-methyl-1H-benzo[d]imidazol-2-yl)thiazole-2,4-diamine (M12)
m. $N^2$-(3-(trifluoromethyl)phenyl)-5-(5-methyl-1H-benzo[d]imidazol-2-yl)thiazole-2,4-diamine (M13)
n. 5-(5-methyl-1H-benzo[d]imidazol-2-yl)-N2-p-tolylthiazole-2,4-diamine (M14)
o. $N^2$-(4-methoxyphenyl)-5-(4-methyl-1H-benzo[d]imidazol-2-yl)thiazole-2,4-diamine (M15)

In another embodiment, the present invention provides a process for synthesis of compounds of formula (I) comprising the steps of:
a) reacting substituted phenyl amine in water with carbon disulfide in presence of suitable base followed by reaction with cyanuric chloride to afford substituted N-Phenyl isothiocynate;
b) reacting N-Phenyl isothiocynate with guanidine in carbon tetrachloride by refluxing the mixture for the period in the range of 2-4 hrs at temperature in the range of 70° C. to 80° C. to afford substituted 1-phenyl-3-formamidinothiocarbamide;
c) refluxing a solution of chloroacetic acid and orthophenylenediamine in HCl for the period in the range of 6-9 hrs at temperature in the range of 90° C. to 100° C. to afford benzimidazole compound;
d) refluxing the solution containing compound of step (b) and compound of step (c) in methanol for the period in the range 4-6 hrs at temperature in the range of 50-70° C. to afford benzimidazole compounds of formula (I).

In preferred embodiment, said substituted phenyl amine compounds in step (a) are selected from phenyl amine, 4-methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine, 4-bromo-2-fluorobenzenamine.

In another preferred embodiment, said substituted N-Phenyl Isothiocynate compounds in step (a) are selected from phenyl isothiocynate, 4-methoxy phenyl isothiocynate, 4-nitro phenyl isothiocynate, 2-nitro phenyl isothiocynate, 4-Chloro phenyl isothiocynate, 2-isothiocyanato-1,3,5-trimethylbenzene, 4-bromo-2-fluoro-1-isothiocyanatobenzene.

In yet another preferred embodiment, said substituted 1-phenyl-3-formamidinothiocarbamide compounds in step (b) are selected from 1-phenyl-3-formamidinothiocarbamide, 4-Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide, 2-Fluro,4-Bromo phenyl-3 formamidinothiocarbamide.

In still another preferred embodiment, said benzoimidazole compound in step (c) is selected from 2-chloromethyl-1H-benzo[d]imidazole, 2-(chloromethyl)-5-methyl-1H-benzo[d]imidazole, 2-(chloromethyl)-4-methyl-1H-benzo[d]imidazole, 2-(chloromethyl)-4-methyl-1H-benzo[d]imidazole.

In further preferred embodiment, said orthophenylenediamine compound in step (c) is selected from benzene-1,2-diamine, 4-methylbenzene-1,2-diamine, 3-methylbenzene-1,2-diamine.

The base as used in step (a) is selected from potassium carbonate.

The 2-chloromethyl-1H-benzo[d]imidazole may be prepared by reacting orthophenylenediamine with chloro acetic acid in presence of hydrochloric acid at ambient temperature.

The synthesis may be conveniently carried out from ambient to reflux temperature of the solvent used in the specific reaction step. The solvents that can be used in the synthesis may be selected from the group ranging from polar to non-polar solvents such as water, $C_1$ to $C_6$ alcohols, hydrocarbons, halogenated hydrocarbons and the like.

The compounds of the invention may comprise one or more chiral centers and hence encompasses its racemates, cis- or trans-isomeric forms and its enantiomers/diastereomers. In yet another embodiment, the invention provides process for synthesis of compounds of formula (I), as per the scheme 1 shown below.

Scheme: 1

Step 1:

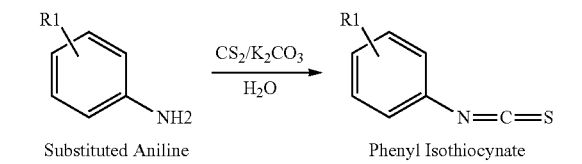

Substituted Aniline          Phenyl Isothiocynate

Step 2:

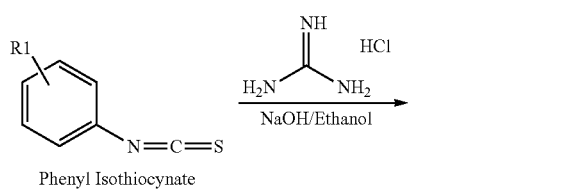

Phenyl Isothiocynate

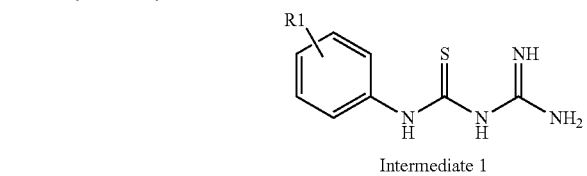

Intermediate 1

Step 3:

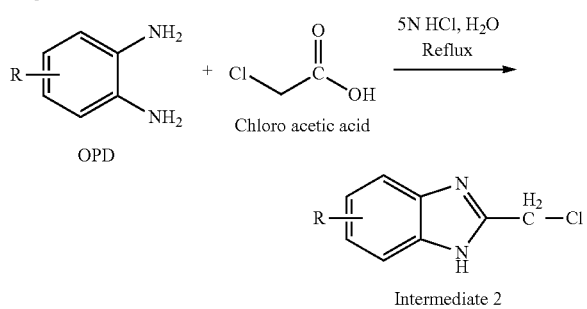

OPD      Chloro acetic acid

Intermediate 2

Step 4:

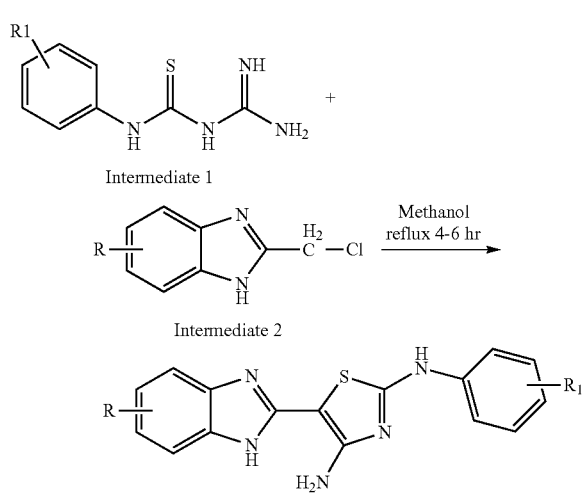

Intermediate 1

Intermediate 2

The compounds of the invention described have been preliminarily screened for their efficacy in treating cancer and related diseases by an in vitro cell proliferation assay against A549 Cell line and U87MG Cell line as exemplified herein below. Other methods will also be apparent to those of ordinary skill in the art.

In one embodiment, the present invention provides a pharmaceutical composition containing an effective amount of compound of formula (I) and at least one pharmaceutical acceptable carrier.

"An effective amount" as mentioned above refers to an amount of a compound of formula (I) that is required to confer a therapeutic effect on the treated subject. Effective doses will vary, as recognized by those skilled in the art, depending on the types of diseases treated, routes of administration, usage of excipients, and the possibility of co-usage with other therapeutic treatments.

The methods of administration of the compounds of the invention include parenteral, oral, nasal, topical, rectal, or buccal administration.

A composition for oral and injectable administration can be a dosage form including capsules, tablets, emulsions and aqueous suspensions, dispersions, and solutions. A composition having one or more active compounds of formula (I) according to the invention can also be administered in the form of suppositories for rectal administration.

The pharmaceutical excipients that may be suitable to administer the compounds of the invention includes binders, fillers, lubricants, disintigrants, oil based and wax based excipients, diluents etc. If desired, certain sweetening, flavoring, or coloring agents can be added to the formulation.

In yet another embodiment, the present invention provides a method for treating abnormal cell growth in mammals comprising administering to the subject an effective amount of compound of formula (I).

"An effective amount" refers herein to an amount of a compound of formula (I) that is required to confer a therapeutic effect on the treated subject. Abnormal cell growth is normally developed in the case of cancers and related diseases. Effective doses will vary, as recognized by those skilled in the art, depending on the types of diseases treated, routes of administration, usage of excipients, and the possibility of co-usage with other therapeutic treatments.

In still another embodiment, the present invention provides compounds of formula (I) for use in the treatment of cancer and related diseases in a subject to confer a therapeutic effect on the treated subject.

The cancer and related disease include the cancers that originated from human organs selected from the group consisting of breast; cervical; colon; lung; head and neck cancer; brain; skin; bone and the like.

The following examples, which include preferred embodiments, will serve to illustrate the practice of this invention, it being understood that the particulars shown are by way of example and for purpose of illustrative discussion of preferred embodiments of the invention.

EXAMPLES

Following examples are given by way of illustration therefore should not be construed to limit the scope of the invention.

Example 1: General Procedure for Preparation of Substituted N-Phenyl Isothiocynate

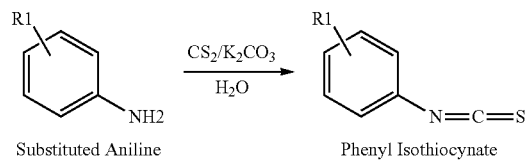

Substituted Aniline      Phenyl Isothiocynate

R1=—H, -4-OCH$_3$, -4-NO$_2$,-2-NO$_2$, -4-Cl, -2,4,6-CH$_3$, -4-CH$_3$, -2-F,4-Br, -4-CF$_3$, -4-S—CH$_3$, -4-Cl,-3-CF$_3$, -3-S—CH$_3$, -3,5-CF$_3$, -2-S—CH$_3$, -3-CF$_3$,-4-OCF$_3$

To a mixture of substituted phenyl amine (20 mmol) and K$_2$CO$_3$ (5.52 g, 40 mmol) in 20 mL of water 1.82 g of CS2 (24 mmol) was added drop wise in a period of 20-30 min at room temperature. After the addition was complete, the mixture was stirred for several hours until complete conversion. Then, the reaction mixture was cooled to 0° C. and a solution of 1.85 g of 1,3,5, cyanuric chloride (Trichloro 2,4,6, triazine (TCT)) (10 mmol) in 15 mL of CH$_2$Cl$_2$ was added drop wise. After the addition was complete, the mixture was stirred for another 0.5 h to finish the reaction. The reaction mixture was then basified to pH>11 with 6 N NaOH to obtain a clear solution. The organic layer was separated and the aqueous phase was extracted with CH$_2$Cl$_2$ (2×10 mL). The combined organic layers were dried over anhydrous Na$_2$SO$_4$, filtered and the solvent was removed.

Using the similar procedure, the following compounds have been prepared as listed in table 1.

TABLE 1

| No. | Compound | R$_1$ | Nature | % Yield | M.P. (° C.) |
|---|---|---|---|---|---|
| 1 | Phenyl isothiocynate | —H | colorless oil | 98 | — |
| 2 | 4-methoxyphenyl isothiocynate | -4-OCH$_3$ | colorless oil | 86 | — |
| 3 | 4-nitro phenyl isothiocynate | -4-NO$_2$ | yellow solid | 13 | 108-110° C. |
| 4 | 2-nitro phenyl isothiocynate | -2-NO$_2$ | yellow solid | 52 | 48-50° C. |
| 5 | 4-Chloro phenyl isothiocynate | -4-Cl | white solid | 92 | 44-45° C. |
| 6 | 2-isothiocyanato-1,3,5-trimethylbenzene | -2,4,6-CH$_3$ | white solid | 90 | 74-76 |
| 7 | 4-bromo-2-fluoro-1-isothiocyanatobenzene | 2-F,-4-Br | Cream Solid | 70 | 88-90 |

Example 2: General Procedure for Preparation of Intermediate 1 (Substituted 1-phenyl-3-formamidinothiocarbamide)

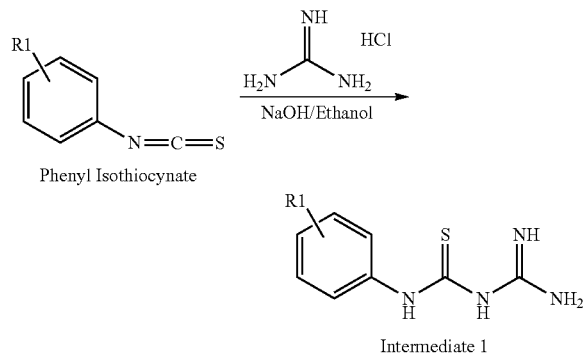

Intermediate 1

R1=—H, -4-OCH$_3$, -4-NO$_2$,-2-NO$_2$, -4-Cl, -2,4,6-CH$_3$, -4-CH$_3$, -2-F,4-Br, -4-CF$_3$, -4-S—CH$_3$, -4-Cl,-3-CF$_3$, -3-S—CH$_3$, -3,5-CF$_3$, -2-S—CH$_3$, -3-CF$_3$,-4-OCF$_3$

A mixture of guanidine (0.01 M) and phenyl isothiocynate (0.01 M) and carbon tetrachloride (50 mL) was refluxed on a water bath for 2 hours. During boiling, the reaction mixture containing the suspended guanidine went into solution and after 1 hour yellowish, needle-shaped crystals gradually separated out. The reaction mixture was then again refluxed for 1 hour then filtered while hot. The new product was dried at room temperature and recrystallized from aqueous ethanol. The reaction scheme for exemplary compounds are shown in above scheme Using the similar procedure, the following compounds have been prepared as listed in table 2.

TABLE 2

| No. | Compound | R$_1$ | % Yield |
|---|---|---|---|
| 1 | 1-phenyl-3-formamidinothiocarbamide | —H | 72 |
| 2 | 4-Methoxy Phenyl-3-formamidinothiocarbamide | -4-OCH$_3$ | 78 |
| 3 | 4-Nitro Phenyl-3-formamidinothiocarbamide | -4-NO$_2$ | 65 |
| 4 | 2-Nitro Phenyl-3-formamidinothiocarbamide | -2-NO$_2$ | 80 |
| 5 | 4-Chloro Phenyl-3-formamidinothiocarbamide | -4-Cl | 82 |
| 6 | 2,4,6-trimethyl Phenyl-3-formamidinothiocarbamide | -2,4,6-CH$_3$ | 86 |
| 7 | 2-Fluro,4-Bromo phenyl-3 formamidinothiocarbamide | 2-F,-4-Br | 74 |

Example 3: General Procedure[3] for Preparation of Intermediate 2 (2-chloromethyl-1H-benzo[d]imidazole)

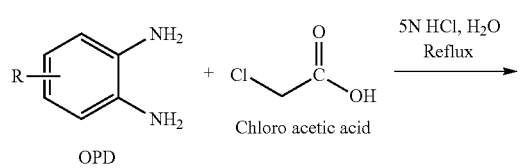

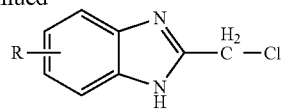

Intermediate 2

R=—H, 3-CH$_3$, 4-NO$_2$, 4-Cl, 2-CH$_3$, 4-CH$_3$, 4-Br, 4-F

In a 250 mL RBF, solution containing 0.08 mole of chloro acetic acid and 0.07 mole of Orthophenylenediamine dissolved in 5 mL of 5N HCl. The mixture was refluxed for 8 hr with constant stirring. The reaction mixture was cooled to 0-5° C. Then Reaction Mixture was neutralized with dilute NaOH solution. The product was filtered and washed with water to remove traces of HCl and dried. It was re-crystallized from benzene:hexane.

Example 4: Preparation of Benzimidazole Compounds of Formula (I)

R=—H, 3-CH$_3$, 4-NO$_2$, 4-Cl, 2-CH$_3$, 4-CH$_3$, 4-Br, 4-F
R1=—H, -4-OCH$_3$, -4-NO$_2$,-2-NO$_2$, -4-Cl, -2,4,6-CH$_3$, -4-CH$_3$, -2-F,4-Br, -4-CF$_3$, -4-S—CH$_3$, -4-Cl,-3-CF$_3$, -3-S—CH$_3$, -3,5-CF$_3$, -2-S—CH$_3$, -3-CF$_3$,-4-OCF$_3$

Substituted phenyl-3-formamidinothiocarbamide (0.01 M) and 2-chloromethyl-1H-benzo[d]imidazole (0.01 M) were refluxed for 4-6 hours in methanol at 60° C. Reaction was monitored by TLC, after completion of reaction Solvent was evaporated by rotary evaporator, and then column was carried out by using silica 60-120, Mobile phase Ethyl acetate:Pet ether (7:3).

Using the similar procedure the following compounds have been prepared as listed in table 3.

TABLE 3

| Sr. No. | Compound Code | Molecular Formula | Molecular Weight | Log P | Yield (%) | M.P. (° C.) |
|---|---|---|---|---|---|---|
| 1 | S2-M1 | C$_{16}$H$_{13}$N$_5$S | 307.09 | 3.02 | 69.80 | 268-270 |
| 2 | S2-M2 | C$_{17}$H$_{15}$N$_5$OS | 337.4 | 2.11 | 54.30 | 224-226 |
| 3 | S2-M3 | C$_{16}$H$_{12}$N$_6$O$_2$S | 352.37 | 3.32 | 65.50 | 260-262 |
| 4 | S2-M4 | C$_{16}$H$_{12}$N$_6$O$_2$S | 352.37 | 3.33 | 66.70 | 220-222 |
| 5 | S2-M5 | C$_{16}$H$_{12}$ClN$_5$S | 341.82 | 3.99 | 77.30 | 210-212 |
| 6 | S2-M6 | C$_{19}$H$_{19}$N$_5$S | 349.45 | 2.11 | 78.20 | 218-220 |
| 7 | S2-M7 | C$_{16}$H$_{11}$BrFN$_5$S | 404.26 | 3.20 | 66.50 | 200-202 |

Example 5

1. Protocol Followed for Anti Cancer Activity and Results, Cell Proliferation Assays: Cell lines used herein were purchased from NCCS (National Center for Cell Sciences) Pune, India. Invitro Activity was performed in NCL (National Chemical Laboratory) Pune. Each cell line was plated in 96-well microtiter plates (10,000 cells per well), and serial dilutions of indicated compounds were added. At the end of the incubation period (72 h at 37° C.), cell viability was determined by a tetrazolium dye, MTT (3-(4,5-dimethylthiazol-2-yl)-2,5-diphenyl tetrazolium bromide) (Promega, USA). The formazan crystals were dissolved in DMSO, and the absorbance at 600 nm was recorded using an ELISA plate reader. IC50 values were calculated using nonlinear regression and defined as the concentration needed for a 50% reduction in absorbance of treated versus untreated control cells.

By using the above procedure, the compounds of the invention were tested on A549 Cell line and the results obtained are presented below in table 4, Refer FIG. 1.

TABLE 4

In-Vitro Anticancer activity against A549 Cell line (Lung Cancer Cell line) (adenocarcinomic human alveolar basal epithelial cells)

| Molecules | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| S4-M1 | 10.9448 | 15.1235 | 29.1210 | 39.0943 | 49.0943 |
| S4-M2 | 51.4651 | 60.4651 | 75.4651 | 89.4651 | 94.9744 |
| S4-M3 | 62.8410 | 71.8410 | 81.8410 | 90.3697 | 97.6429 |
| S4-M4 | 18.4286 | 25.8703 | 34.6810 | 49.0516 | 57.0586 |
| S4-M5 | 54.9487 | 65.9487 | 73.9487 | 85.5791 | 95.8393 |
| S4-M6 | 50.0435 | 61.0435 | 72.0435 | 85.1263 | 92.3214 |
| S4-M7 | 62.7909 | 71.7909 | 81.7909 | 90.9283 | 97.0714 |
| S4-M8 | 59.5611 | 68.5611 | 76.5611 | 88.7952 | 98.6071 |
| S4-M9 | 48.3118 | 57.3118 | 68.3118 | 79.8430 | 88.9887 |
| S4-M10 | 49.3915 | 61.3915 | 70.3915 | 81.0148 | 90.9286 |
| S4-M11 | 51.8332 | 63.8332 | 72.8332 | 80.6860 | 94.7857 |
| S4-M12 | 49.9492 | 58.9492 | 69.9492 | 81.3561 | 93.1429 |
| S4-M13 | 50.6358 | 61.6358 | 73.6358 | 82.9272 | 99.4107 |
| S4-M14 | 51.1210 | 62.1210 | 71.1210 | 84.1126 | 96.0357 |
| S4-M15 | 49.3067 | 59.3067 | 68.3067 | 79.6507 | 93.1071 |
| Gefitinib | 20.3067 | 29.3067 | 35.3067 | 43.6507 | 55.2143 |

Table 4 indicates anticancer activity against A549 Cell line. The Gefitinib was used as standard and % cell Viable was measured compared to control. The procedure used was MTT assay as mentioned. The most active among 15 molecules were M1 and M4. By using the above procedure, the compounds of the invention were tested on MCF-7 Cell line and the results obtained are presented below in table 5, Refer FIG. 2.

TABLE 5

In-Vitro Anticancer activity against MCF-7 Cell line

| Molecules | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| S4-M1 | 30.9447 | 42.5976 | 49.1210 | 60.3781 | 69.7814 |
| S4-M2 | 84.4651 | 90.4651 | 95.4651 | 95.4651 | 96.9744 |
| S4-M3 | 72.8410 | 84.8410 | 90.8410 | 92.3697 | 99.6429 |
| S4-M4 | 31.8571 | 42.8717 | 53.8168 | 61.1561 | 72.7083 |
| S4-M5 | 65.9487 | 72.9487 | 79.9487 | 83.5791 | 89.8393 |
| S4-M6 | 100.4350 | 100.0435 | 101.0435 | 100.1263 | 112.3214 |
| S4-M7 | 100.7909 | 100.7909 | 100.7909 | 100.9283 | 100.0714 |
| S4-M8 | 69.5611 | 79.5611 | 82.5611 | 90.7952 | 98.6071 |
| S4-M9 | 96.6358 | 96.3118 | 96.3118 | 98.8430 | 99.9887 |
| S4-M10 | 100.3915 | 100.3915 | 104.3915 | 120.0148 | 140.9286 |
| S4-M11 | 100.8332 | 100.8332 | 110.2404 | 132.6860 | 156.7857 |
| S4-M12 | 70.7987 | 74.9492 | 85.9492 | 91.3561 | 99.1429 |
| S4-M13 | 66.9492 | 72.6358 | 81.3581 | 92.9272 | 99.4107 |
| S4-M14 | 65.1210 | 69.2621 | 83.6213 | 90.1126 | 94.0357 |
| S4-M15 | 61.3067 | 70.6748 | 75.7485 | 89.9477 | 92.1071 |
| Gefitinib | 20.3067 | 29.3067 | 35.3067 | 43.6507 | 55.2143 |

Table 5 indicates anticancer activity against MCF-7 Cell line. The Gefitinib was used as standard and % cell Viable was measured compared to control. The procedure used was MTT assay as mentioned. The most active among 15 molecules were M1 and M4.

By using the above procedure, the compounds of the invention were tested on HOP-62 Cell line and the results obtained are presented below in table 6, Refer FIG. 3.

TABLE 6

In-Vitro Anticancer activity against HOP-62 Cell line

| Molecules | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| S4-M1 | 12.9448 | 22.1235 | 34.1210 | 42.0943 | 54.0943 |
| S4-M2 | 75.4651 | 77.4651 | 85.4651 | 93.4651 | 98.9744 |
| S4-M3 | 88.8410 | 90.8410 | 90.8410 | 94.3697 | 99.6429 |
| S4-M4 | 12.4286 | 18.8703 | 25.6810 | 36.0516 | 43.0586 |
| S4-M5 | 75.9487 | 82.9487 | 88.9487 | 92.5791 | 100.8123 |
| S4-M6 | 90.9760 | 100.3503 | 100.2510 | 100.1263 | 103.3214 |
| S4-M7 | 90.8533 | 100.3185 | 100.1846 | 100.9283 | 102.0714 |
| S4-M8 | 80.5611 | 81.5611 | 89.5611 | 90.7952 | 99.6071 |
| S4-M9 | 90.7987 | 98.3118 | 100.3118 | 100.8430 | 122.9887 |
| S4-M10 | 89.3915 | 95.3915 | 99.3915 | 100.0148 | 103.9286 |
| S4-M11 | 91.8332 | 96.8332 | 98.2404 | 100.6860 | 156.7857 |
| S4-M12 | 79.9492 | 85.9492 | 92.9492 | 95.3561 | 102.1429 |
| S4-M13 | 75.6358 | 80.6358 | 90.3581 | 96.9272 | 99.4107 |
| S4-M14 | 80.1210 | 88.2621 | 93.6213 | 95.1126 | 101.0357 |
| S4-M15 | 77.3067 | 81.6748 | 92.7485 | 98.6507 | 104.1071 |
| Gefitinib | 20.3067 | 29.3067 | 35.3067 | 43.6507 | 55.2143 |

Table 6 indicates anticancer activity against HOP-62 Cell line. The Gefitinib was used as standard and % cell Viable was measured compared to control. The procedure used was MTT assay as mentioned. The most active among 15 molecules were M1 and M4.

Figure 4:
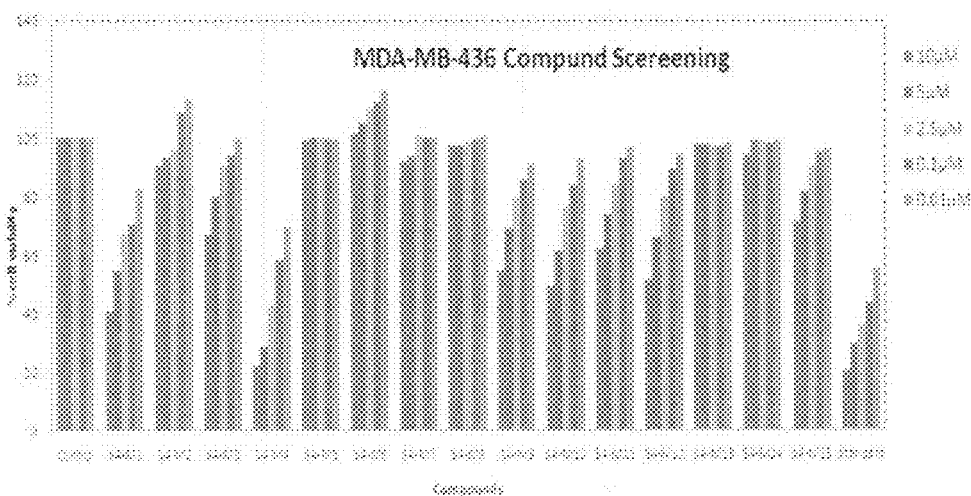
FIG. 4: In vitro screening of Benzimidazole derivatives against MDA-MB-436 cell line indicates % cell Viability after administrating various concentration of synthesized molecules on MDA-MB 436 cell line. 5 dose concentrations were taken in to consideration to find out exact IC50.

By using the above procedure, the compounds of the invention were tested on MDA-MB-436 Cell line and the results obtained are presented below in table 7, Refer FIG. 4.

TABLE 7

In-Vitro Anticancer activity against MDA-MB-436 Cell line

| Molecules | % cell viability | | | | |
|---|---|---|---|---|---|
| | 10 µM | 5 µM | 2.5 µM | 0.1 µM | 0.01 µM |
| Control | 100 | 100 | 100 | 100 | 100 |
| S4-M1 | 40.9447 | 54.5976 | 67.1210 | 70.3781 | 82.7814 |
| S4-M2 | 90.4651 | 93.4651 | 95.4651 | 108.4651 | 112.9744 |
| S4-M3 | 66.8410 | 79.8410 | 90.8410 | 94.3697 | 99.6429 |
| S4-M4 | 21.8571 | 28.8717 | 42.8168 | 58.1561 | 69.7083 |
| S4-M5 | 98.9487 | 99.9487 | 99.9487 | 99.5791 | 99.8393 |
| S4-M6 | 101.4350 | 105.0435 | 110.0435 | 112.1263 | 116.3214 |
| S4-M7 | 91.7909 | 93.7909 | 100.7909 | 99.9283 | 100.0714 |
| S4-M8 | 97.5611 | 97.5611 | 98.5611 | 99.7952 | 100.6071 |
| S4-M9 | 54.6358 | 69.3118 | 79.3118 | 85.8430 | 90.9887 |
| S4-M10 | 49.3915 | 61.3915 | 76.3915 | 84.0148 | 92.9286 |
| S4-M11 | 61.8332 | 73.8332 | 84.2404 | 92.6860 | 96.7857 |
| S4-M12 | 51.7987 | 65.9492 | 79.9492 | 89.3561 | 94.1429 |
| S4-M13 | 97.9492 | 97.6358 | 97.3581 | 96.9272 | 98.4107 |
| S4-M14 | 94.1210 | 99.2621 | 98.6213 | 98.1126 | 99.0357 |
| S4-M15 | 71.3067 | 81.6748 | 90.7485 | 94.9477 | 96.1071 |
| Gefitinib | 20.3067 | 29.3067 | 35.3067 | 43.6507 | 55.2143 |

Table 7 indicates anticancer activity against MDA-MB-436 Cell line. The Gefitinib was used as standard and % cell Viable was measured compared to control. The procedure used was MTT assay as mentioned. The most active among 15 molecules were M1 and M4.

Figure 5:
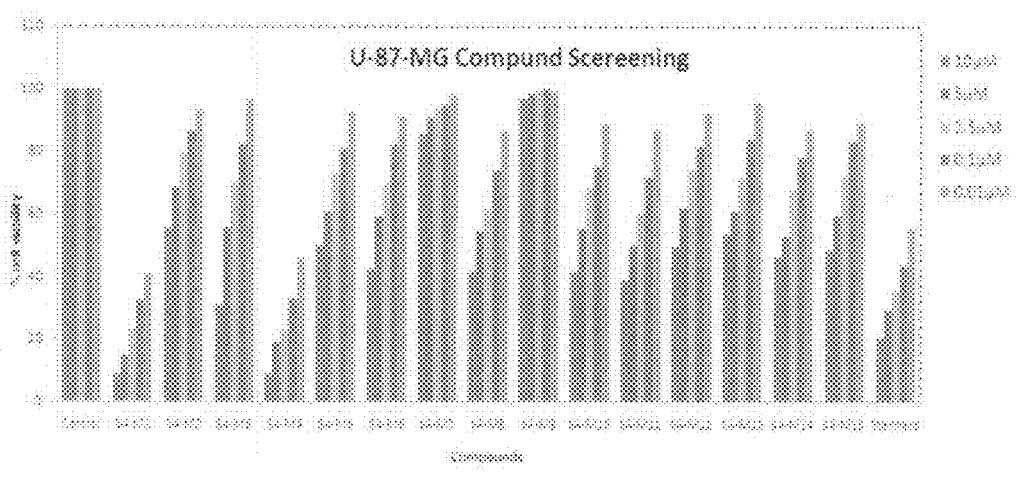
FIG. 5: In vitro screening of Benzimidazole derivatives against U-87-MG cell line indicates % cell Viability after administrating various concentration of synthesized molecules on U-87-MG cell line. 5 dose concentrations were taken in to consideration to find out exact IC50.

By using the above procedure, the compounds of the invention were tested on U87MG Cell line (glioblastoma cell line) and the results obtained are presented below in table 8, Refer FIG. 5.

TABLE 8

In-Vitro Anticancer activity against U87MG Cell line (Glioblastoma cell line)

| Molecules | % cell viability | | | | |
|---|---|---|---|---|---|
| | 10 μM | 5 μM | 2.5 μM | 0.1 μM | 0.01 μM |
| Control | 100 | 100 | 100 | 100 | 100 |
| S4-M1 | 8.9447 | 14.5976 | 23.1210 | 32.3781 | 40.7814 |
| S4-M2 | 55.4651 | 68.4651 | 79.4651 | 86.4651 | 92.9744 |
| S4-M3 | 30.8410 | 55.8410 | 69.8410 | 82.3697 | 96.6429 |
| S4-M4 | 8.8571 | 18.8717 | 22.8168 | 33.1561 | 45.7083 |
| S4-M5 | 49.9487 | 60.9487 | 72.9487 | 80.5791 | 92.8393 |
| S4-M6 | 42.4350 | 59.0435 | 70.0435 | 82.1263 | 91.3214 |
| S4-M7 | 85.7909 | 90.7909 | 93.7909 | 94.9283 | 98.0714 |
| S4-M8 | 41.5611 | 54.5611 | 61.5611 | 73.7952 | 86.6071 |
| S4-M9 | 96.9492 | 98.6358 | 99.3581 | 99.9272 | 99.4107 |
| S4-M10 | 41.3915 | 55.3915 | 68.3915 | 75.0148 | 88.9286 |
| S4-M11 | 38.8332 | 49.8332 | 60.2404 | 71.6860 | 86.7857 |
| S4-M12 | 49.7987 | 61.9492 | 73.9492 | 81.3561 | 92.1429 |
| S4-M13 | 53.8332 | 60.8332 | 71.2404 | 83.6860 | 95.7857 |
| S4-M14 | 46.1210 | 53.2621 | 67.6213 | 78.1126 | 87.0357 |
| S4-M15 | 48.3067 | 59.6748 | 71.7485 | 82.9477 | 89.1071 |
| Gefitinib | 20.3067 | 29.3067 | 35.3067 | 43.6507 | 55.2143 |

Table 8 indicates anticancer activity against U87-MG Cell line. The Gefitinib was used as standard and % cell Viable was measured compared to control. The procedure used was MTT assay as mentioned. The most active among 15 molecules were M1 and M4.

The all figures were showing % cell viability after administrating various concentrations of total 15 molecules like 10 micro mole, 5 micromole 2.5 micromole, 0.1 micro moles, 0.01 micro moles respectively. The Standard used in all Cases was Gefitinib which is EGFR inhibitor, and we compare the Invitro activity with the Gefitinib. The most active compound is M1 and M4 against A549 cell line. M1 contains no substitution means R is —H and R1 is also —H. but in M4 R is —H and $R_1$ is also —$NO_2$. But other molecules showing less activity as compared to Gefitinib. Against MCF-7 cell line again M1 and M4 are showing Invitro activity, means they are showing antitumor activity against MCF-7 like as shown in all figure. Against HOP62 and MDA-MB-436 cell line also, remove only M1 and M4 are showing Invitro activity comparable to standard Gefitinib on small range of concentration i.e. micro molar concentration. The values on respective tables are showing the % cell viable after administration of synthesized compound on various concentrations.

ADVANTAGES OF THE PRESENT INVENTION

1. New anti cancer compounds provided
2. The compounds possess good anti cancer efficacy
3. The process of synthesis is simple

We claim:
1. A compound of formula (I)

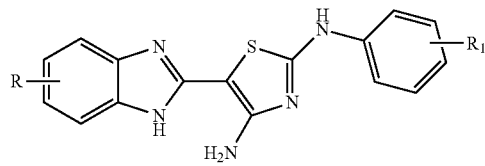

Formula (I)

wherein, R=—H, 3-$CH_3$, 4-$NO_2$, 4-Cl, 2-$CH_3$, 4-$CH_3$, 4-Br or 4-F; and $R_1$=—H, -4-$OCH_3$, -4-$NO_2$,-2-$NO_2$, -4-Cl, -2,4,6-$CH_3$, -4-$CH_3$, -2-F,4-Br, -4-$CF_3$, -4-S—$CH_3$, -4-Cl,-3-$CF_3$, -3-S—$CH_3$, -3,5-$CF_3$, -2-S—$CH_3$, -3-$CF_3$,-4-$OCF_3$, —Si—$(CH_3)_3$, —Si—$(C_2H_5)_3$ or $(CH_3)_2$—Si— $C_2H_5$.

2. The compound as claimed in claim 1, wherein said compound is selected from the group consisting of:
   i. 5-(1H-benzo[d]imidazol-2-yl)-$N^2$-phenylthiazole-2,4-diamine (M1);
   ii. 5-(1H-benzo[d]imidazol-2-yl)-$N^2$-(4-methoxyphenyl) thiazole-2,4-diamine (M2);
   iii. 5-(1H-benzo[d]imidazol-2-yl)-$N^2$-(4-nitrophenyl)thiazole-2,4-diamine (M3);
   iv. 5-(1H-benzo[d]imidazol-2-yl)-$N^2$-(2-nitrophenyl)thiazole-2,4-diamine (M4);
   v. 5-(1H-benzo[d]imidazol-2-yl)-$N^2$-(4-chlorophenyl)thiazole-2,4-diamine (M5);
   vi. 5-(1H-benzo[d]imidazol-2-yl)-$N^2$-mesitylthiazole-2,4-diamine (M6);
   vii. 5-(1H-benzo[d]imidazol-2-yl)-$N^2$-(4-bromo-2-fluorophenyl)thiazole-2,4-diamine (M7);
   viii. 5-(1H-benzo[d]imidazol-2-yl)-N2-(3-(trifluoromethyl)phenyl)thiazole-2,4-diamine (M8);
   ix. 5-(1H-benzo[d]imidazol-2-yl)-N2-p-tolylthiazole-2,4-diamine (M9);
   x. 5-(5-methyl-1H-benzo[d]imidazol-2-yl)-N2-phenylthiazole-2,4-diamine (M10);
   xi. $N^2$-(4-methoxyphenyl)-5-(5-methyl-1H-benzo[d]imidazol-2-yl)thiazole-2,4-diamine (M11);
   xii. $N^2$-(4-chlorophenyl)-5-(5-methyl-1H-benzo[d]imidazol-2-yl)thiazole-2,4-diamine (M12);
   xiii. $N^2$-(3-(trifluoromethyl)phenyl)-5-(5-methyl-1H-benzo[d]imidazol-2-yl)thiazole-2,4-diamine (M13);
   xiv. 5-(5-methyl-1H-benzo[d]imidazol-2-yl)-N2-p-tolylthiazole-2,4-diamine (M14) and
   xv. $N^2$-(4-methoxyphenyl)-5-(4-methyl-1H-benzo[d]imidazol-2-yl)thiazole-2,4-diamine (M15).

3. A process for the preparation of compounds of formula (I) as claimed in claim 1, wherein said process comprising the steps of:
   a) reacting substituted phenyl amine in water with carbon disulfide in presence of a suitable base followed by reaction with cyanuric chloride to afford substituted N-Phenyl isothiocyanate;
   b) reacting N-Phenyl isothiocyanate with guanidine in carbon tetrachloride by refluxing the mixture for the period in the range of 2-4 hrs at a temperature in the range of 70 to 80° C. to afford substituted 1-phenyl-3-formamidinothiocarbamide;
   c) refluxing a solution of chloro acetic acid and ortho-phenylenediamine compound in HCl for the period in the range of 6-9 hrs at a temperature in the range of 90 to 100° C. to afford benzoimidazole compound; and
   d) refluxing the solution containing compound of step (b) and compound of step (c) in a solvent for the period in the range of 4-6 hrs at a temperature in the range of 50-70° C. to afford benzimidazole compounds of formula (I).

4. The process as claimed in claim 3, wherein said substituted phenyl amine compounds are selected from 4 methoxy phenyl amine, 4-nitro phenyl amine, 2-nitro phenyl amine, 4-Chloro phenyl amine, 3-(trifluoromethyl) benzenamine, 3,5-bis (trifluoromethyl) benzenamine, 4-(trifluoromethoxy) benzenamine, 2,4,6-trimethylbenzenamine and 4-bromo-2-fluorobenzenamine.

5. The process as claimed in claim 3, wherein said substituted N-Phenyl isothiocyanate compound is selected from 4-methoxy phenyl isothiocyanate, 4-nitro phenyl isothiocyanate, 2-nitro phenyl isothiocyanate, 4-Chloro phenyl isothiocyanate, 2-isothiocyanato-1,3,5-trimethylbenzene and 4-bromo-2-fluoro-1-isothiocyanatobenzene.

6. The process as claimed in claim 3, wherein said substituted 1-phenyl-3-formamidinothiocarbamide compound is selected from 4 Methoxy Phenyl-3-formamidinothiocarbamide, 4-Nitro Phenyl-3-formamidinothiocarbamide, 2-Nitro Phenyl-3-formamidinothiocarbamide, 4-Chloro Phenyl-3-formamidinothiocarbamide, 2,4,6-trimethyl Phenyl-3-formamidinothiocarbamide and 2-Fluro,4-Bromo phenyl-3 formamidinothiocarbamide.

7. The process as claimed in claim 3, wherein said benzoimidazole compound in step (c) is selected from the group consisting of 2-chloromethyl-1H-benzo[d]imidazole, 2-(chloromethyl)-5-methyl-1H-benzo[d]imidazole, 2-(chloromethyl)-4-methyl-1H-benzo[d]imidazole and 2-(chloromethyl)-4-methyl-1H-benzo[d]imidazole.

8. The process as claimed in claim 3, wherein said orthophenylenediamine compound in step (c) is selected from benzene-1,2-diamine, 4-methylbenzene-1,2-diamine or 3-methylbenzene-1,2-diamine.

9. The process as claimed in claim 3, wherein said base in step (a) is potassium carbonate.

10. A pharmaceutical composition comprising compound of formula (I) as claimed in claim 1 and at least one pharmaceutically acceptable carrier.

11. A method for treating abnormal cell growth developed from lung cancer, breast cancer and brain cancer in mammals in a subject, which comprises administering a therapeutically effective amount of the compound of formula (I) as claimed in claim 1 to the subject in association with at least one pharmaceutical acceptable carrier or diluents or excipient.

12. The method as claimed in claim 11, wherein said subject is human.

* * * * *